United States Patent [19]

James et al.

[11] 4,110,918
[45] Sep. 5, 1978

[54] MODULAR BIOFEEDBACK TRAINING SYSTEM

[75] Inventors: J. Michael James, Cambridge; James F. Fee, Needham; Richard M. Horton, Duxbury, all of Mass.

[73] Assignee: Cyborg Corporation, Brighton, Mass.

[21] Appl. No.: 707,295

[22] Filed: Jul. 21, 1976

[51] Int. Cl.² .............................................. G09B 19/00
[52] U.S. Cl. .................................. 35/22 R; 128/2 H; 128/2.1 B
[58] Field of Search ............................... 35/22 R, 22; 128/2.05 R, 2.06 R, 2.1 B, 2.1 M, 2 H, 2.1 Z, 2.05, 2.06, 2.1; 235/151.30, 151.34

[56] References Cited

U.S. PATENT DOCUMENTS

| | | | |
|---|---|---|---|
| 3,821,949 | 7/1974 | Hartzel et al. | 128/2.1 B |
| 3,875,930 | 4/1975 | Silva et al. | 128/2.1 B |
| 3,882,850 | 5/1975 | Baiun | 128/2.1 B |
| 3,905,355 | 9/1975 | Brudny | 128/2.1 M |
| 3,910,258 | 10/1975 | Pisarski et al. | 128/2.1 B |
| 3,942,516 | 3/1976 | Glynn et al. | 128/2.1 B |
| 3,978,847 | 9/1976 | Fehmi et al. | 128/2.1 B |
| 3,991,304 | 11/1976 | Hillsman | 128/2.08 |

OTHER PUBLICATIONS

*Popular Electronics*; "Build a Muscle Feedback Monitor"; May, 1975; pp. 39–42.

*Primary Examiner*—Vance Y. Hum
*Attorney, Agent, or Firm*—Morse, Altman, Oates & Bello

[57] ABSTRACT

A biofeedback training system is provided in which portable, self-contained modular units may be used independently for relatively simple biofeedback training purposes by a layman or may be connected to a central processor adapted to provide more sophisticated processing of the signals monitored by the portable unit under supervision of a specialist. The system thus provides a partitioning of functions in which physiological signals are monitored and preprocessed in the portable unit, and when the portable unit is connected to the central processor, these preprocessed signals are then fed into the central processor where elaborate filtering, thresholding, converting and integrating functions take place in a biofeedback system. The central processor is capable of receiving inputs simultaneously from multiple portable units. The portable unit is characterized by a compact, lightweight housing featuring adjustable threshold settings, automatic electrode and battery checking circuits, multiple mode audio feedback and shaping controls. The signal preconditioning circuits at the input side of the portable unit include amplification and filtering stages of a design capability matched to the central processor and exceeding the requirements of the portable unit but compatible with both the central processor and portable unit.

15 Claims, 5 Drawing Figures

MODULAR BIOFEEDBACK TRAINING SYSTEM

BACKGROUND OF THE INVENTION

1. Field of the Invention

This invention relates generally to biofeedback training systems and more particularly is directed towards a new and improved modular biofeedback training system comprised of one or more individual, self-contained independently operable portable biofeedback training units and a central processor to which one or more units may be connected to provide additional signal processing capability.

2. Description of the Prior Art

Biofeedback instrumentation has been developed in recent years to serve as an aid to persons attempting to achieve control over autonomic body functions. By way of example, it is known that the electrical resistance in the skin of humans varies as a function of autonomic nervous system activity. The change in skin resistance occurs as the result of autonomic activity which has been demonstrated to be generalized and not merely of a local character. For example, an individual who has been involved in a stress situation will display a sudden drop in resistance between two areas of the skin. A measurement of this change in skin resistance is useful not only in research but also to provide a physician or the subject himself with an indication of stress levels. With practice, this knowledge can be used by the subject to control the autonomic activity which gave rise to the change in resistance. Many other autonomic conditions can be monitored and controlled through biofeedback instrumentation and training, including body temperatures (thermal), brainwave activity (EEG) and muscle neuron activity (EMG), for example.

Biofeedback instrumentation heretofore has involved instruments of various levels of sensitivity and function depending upon the particular application and the level of interest of the user. Cost has also been a factor in determining the capabilities of equipment provided.

Biofeedback instruments heretofore have been built with specific fixed capabilities which do not lend themselves to increasing their capability except by elaborate modification.

Accordingly, it is an object of the present invention to provide a modular biofeedback training system in which functional components are partitioned and optionally connectable so that portable units of a given capability may be used independently or in conjunction with a more elaborate processing station. Another object of this invention is to provide a small, portable, completely self-contained biofeedback unit which may be used by itself or in conjunction with a main processor. A more general object of this invention is to provide improvements in biofeedback instrumentation.

SUMMARY OF THE INVENTION

This invention features a modular biofeedback training system comprising a central processing station adapted to connect with one or more modular, self-contained portable biofeedback units each of which may be used by itself as an independent instrument or in conjunction with the central station. The central processor is characterized by circuitry for the elaborate filtering, thresholding, converting and integrating of signals which have been preprocessed by the portable units. The portable unit includes signal preconditioning circuits at the input section thereof comprised of amplification and filtering stages of a design capability matched to the central processor and exceeding the functional requirements of the portable unit but compatible with both. The units are optically coupled to the central processor when in the system mode. The individual portable units provide biofeedback instrumentation of a less elaborate nature than the central processor but feature multiple automatic circuits to insure proper operation in addition to shaping controls to alter training goals.

DETAILED DESCRIPTION OF THE PREFERRED EMBODIMENTS

Figure 1:
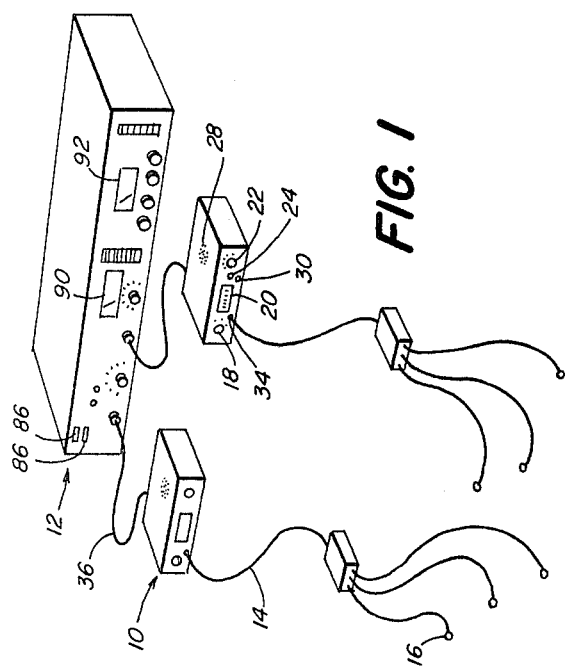
FIG. 1 is a view in perspective of a modular biofeedback training system made according to the invention.

Referring now to the drawings, the reference character 10 generally indicates a self-contained, portable biofeedback training unit which may be used by itself or in conjunction with a central processor 12. When used by itself, the unit 10 serves as a completely self-contained training unit which, in the illustrated embodiment, monitors and processes EMG signals. The unit 10 is primarily intended as a muscle trainer for use in physical therapy, occupational therapy and home training applications. The unit 10 is battery operated and is capable of detecting a single motor activity on a patient through the means of leads 14 terminating in electrodes 16 which are attached to different points on the skin of the subject. The function of the spaced electrodes is to provide a circuit to different points on the skin in order that the muscle neuron activity in the area may be measured and any change in activity monitored to provide an input signal to the unit 10.

The unit 10 is adapted to sense changes in muscle neuron activity and to provide biofeedback signals to the patient within several ranges of sensitivity, typically from 0.1 uv to over 1000 uv. In the illustrated embodiment, three overlapping ranges may be set into the instrument by means of a dial 18 which also functions as the on-off switch. The instrument also includes a logarithmic meter 20 providing increased resolution as the EMG level drops. This meter is used in conjunction with a shaping control knob 22 used to alter training goals and to indicate the level of EMG activity. The knob is calibrated for threshold training techniques. A switch 24 on the unit 10 is used to alter the audiofeedback selectively from a variable tone to a variable click rate, as desired. The audio feedback is delivered through a speaker 26 mounted within the housing behind perforations 28 in the top wall of the housing.

A light 30, typically a light emitting diode, is provided on the front of the unit which serves a double function, one of which includes a warning indicator in the event of a faulty sensor contact, and the other of which is to warn when the power level of the batteries 32 drops to a point that they require replacement or recharging. The lead 14 connects to the unit 10 by means of a jack 34, which jack also serves to receive a recharging lead, not shown, so that the unit cannot be used while it is being recharged. This prevents any possibility of a patient being shocked through a short circuit as the unit is recharging.

As a further protective measure, the unit 10 connects to the central processor 12 by a lead 36 which is optically coupled by means of an optical isolator 38. The optical isolator serves to eliminate any electrical continuity between the central processor 12 and the portable unit 10 insofar as the unit functions with only a beam of light carrying information between the two sections. In this fashion, a malfunction in one unit is isolated and cannot affect the safety of the other unit.

Figure 2:
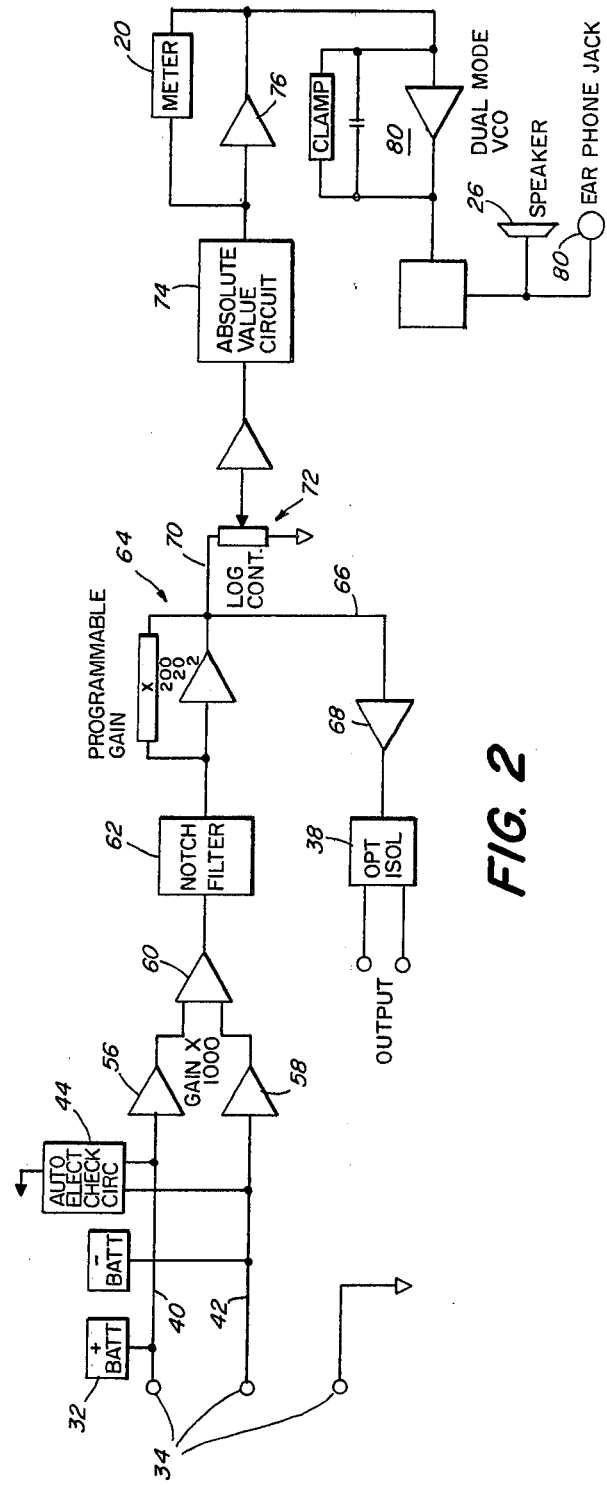
FIG. 2 is a block diagram of the functional components in each portable unit.
Figure 3:
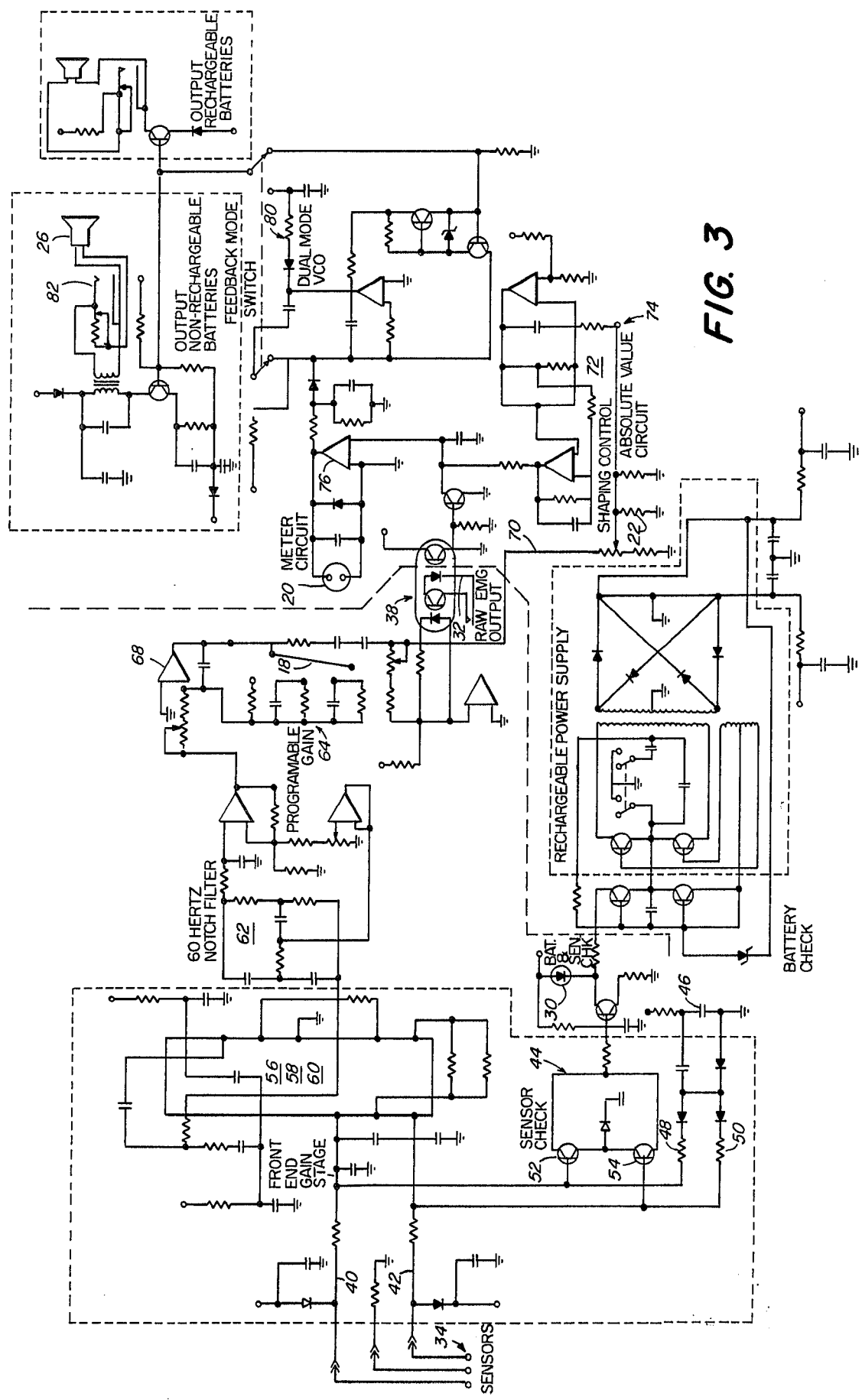
FIG. 3 is a schematic diagram of the circuitry employed in the portable unit.

Referring now to FIG. 2, the functional components are illustrated in block form for the unit 10. As shown, signals sensed by the electrodes 16 are fed into the unit at the jack contacts 34 which run in parallel and connect to the battery 32. The battery 32 may be rechargeable or replaceable as desired. Connected across leads 40 and 42 is an automatic electrode checking circuit 44, the function of which is to verify that a good contact has been made by the electrodes 16. If the electrodes are not properly connected, the circuit 44 will cause the indicator light 30 to be illuminated. The circuit will also cause the light 30 to be illuminated in the event that the battery power drops to too low a level for the circuit to operate properly. This circuit 44, which in essence is a warning circuit, is reset each time the unit is used. The warning circuit 44 operates by sensing the voltage drop across the electrodes. When the unit is first turned on, the indicator light automatically goes on if the electrodes are not properly connected. When the unit is switched on a charge is placed on a capacitor 46 (FIG. 3). This charge is applied across resistors 48 and 50 and current is sent out to the electrodes 16 via the leads 40 and 42. The voltage drop across these two leads is sensed, and if it exceeds a threshold level, the warning light 30 is turned on indicating poor electrode contact and high resistance. After the capacitors 46 discharge, the circuit is then set up so that the sensor is put out of the circuit and the resistor will not later appear in the circuit. The warning circuit includes a pair of transistors 52 and 54 which function to sense the voltage drop and, when biased, cause the light 30 to go on. The same light 30 will be energized in the event that the battery power drops too low by the action of the same transistors 52 and 54.

The leads 40 and 42 feed into a pair of amplifiers 56 and 58, both of which feed into a third amplifier 60. The amplifying stages provide a gain typically on the order of 1000 and is identified as the front end gain stage. The high gain is required because of the low power level of the signals being fed into the unit from the electrodes and also to precondition the signal for the central processor 12. The output of the amplifier 60 is fed into a filter 62 which, in the illustrated system, is a 60 Hz notch filter. The filter has a bandwidth of 100 to 1000 Hz characterized by rejection of 60 Hz pulses.

From the notch filter 62, the signal is then fed through a programmable gain stage 64, typically providing gain on the order of 2,000, 20,000 and 200,000. This gain is set in by means of adjustment to the dial 18 which switches in the desired gain.

From the gain stage 64, the output is fed to one of two possible paths, one being along a lead 66 through an amplifier 68, then to the optical isolator 38 where the signal is electro-optically coded and transmitted by the lead 36 to the main processor 12 for further and more sophisticated processing. Where the unit is used by itself without the central processor, the signal from the stage 64 is fed by a lead 70 through a logarithmic control stage 72 which is controlled by means of the dial 22. The logarithmic control stage provides a variable gain ranging from x1 to x100.

From the logarithmic control stage 72, the signal is then passed through an absolute value circuit 74, thence through an amplifier 76 and the meter 20 which is connected across the amplifier 76. The signal is then fed into a dual-mode, voltage-controlled oscillator stage 80 which drives the speaker 26 as well as a jack 82 should earphones be used with the instrument.

Using the unit 10 alone, an individual may monitor his own muscle neuron activity (EMG biofeedback). The unit allows the monitoring of deep muscle relaxation as low as 0.7 microvolts, with the feedback signals being presented both visually on the meter 20 as well as audibly through the speaker 26. The meter allows comparison with pre-established goals, which may be set on the meter 20, and provides information as to the exact EMG level being monitored. For example, the user might set the instrument at 4 and if the meter reads at the x1 or center position then the user has met the goal of 4 since the incoming signal is compared with the preset level.

The circuitry filters out electrical noise and passes only a signal which is within the bandpass characteristics of the filter, all other signals being rejected. When the unit is first operated, the needle on the meter 20 is centered by adjusting the dials and the actual reading is determined by multiplying the needle reading by whatever setting is on the dial. The audio feedback is selectively provided by clicks which repeat at a fast or slow rate according to changes in the signal, or, alternatively, by a tone the pitch of which changes with the signal.

When more refined information is to be obtained from the subject, the unit is connected to the central processor 12 which has greater filtering capability and other more sophisticated functions. When the unit is plugged into the central processor, that portion of the unit 10 beyond the programmable gain stage 64 is bypassed. In some instances two similar units 10 may be used, as suggested in FIG. 1, both units being connected to the same central processor 12.

The central processing circuitry provides better filtering as well as greater enhancement of the preconditioned signal, thereby providing a better signal-to-noise ratio. The central processor 12 is capable of making highly precise measurements of the incoming signals by using root - mean - square (RMS) techniques. This feature is particularly useful in measuring signals with the characteristics of muscle neuron activity. The processor 12 can accept an amplified version of a signal to provide additional signal conditioning and is adapted to feed the signal back in various feedback modes or control external equipment, such as recorders in analog or binary form, for example, depending upon the requirements of the subject or the clinician supervising the equipment.

The processor 12 is able to generate a wide variety of feedback modes such as tone signals, clicks, variable pitch tone signals, variable repetition rate, and the like. Also, derivative feedback signals can be obtained only if the signal is increasing and inverted if the signal is decreasing. In such situations the variable repetition rate and the pitch increase. In all, nine feedback modes are possible, including four modes, each of which can be inverted if the signal is decreasing and a raw feedback mode in which the raw amplified signal is fed back.

In the processor 12, a predetermined threshold can be set and the circuitry will respond so that a feedback signal is generated if the monitored signal exceeds either an upper or a lower threshold. Also, two of the units 10 may be connected to a single processor 12, thereby forming two channels. The threshold for one channel set at one level and the other channel at a different level to inhibit feedback signals in the first channel. This arrangement allows the system to be used in the training of different parts of the body, especially where the body parts interact with one another.

Figure 4:
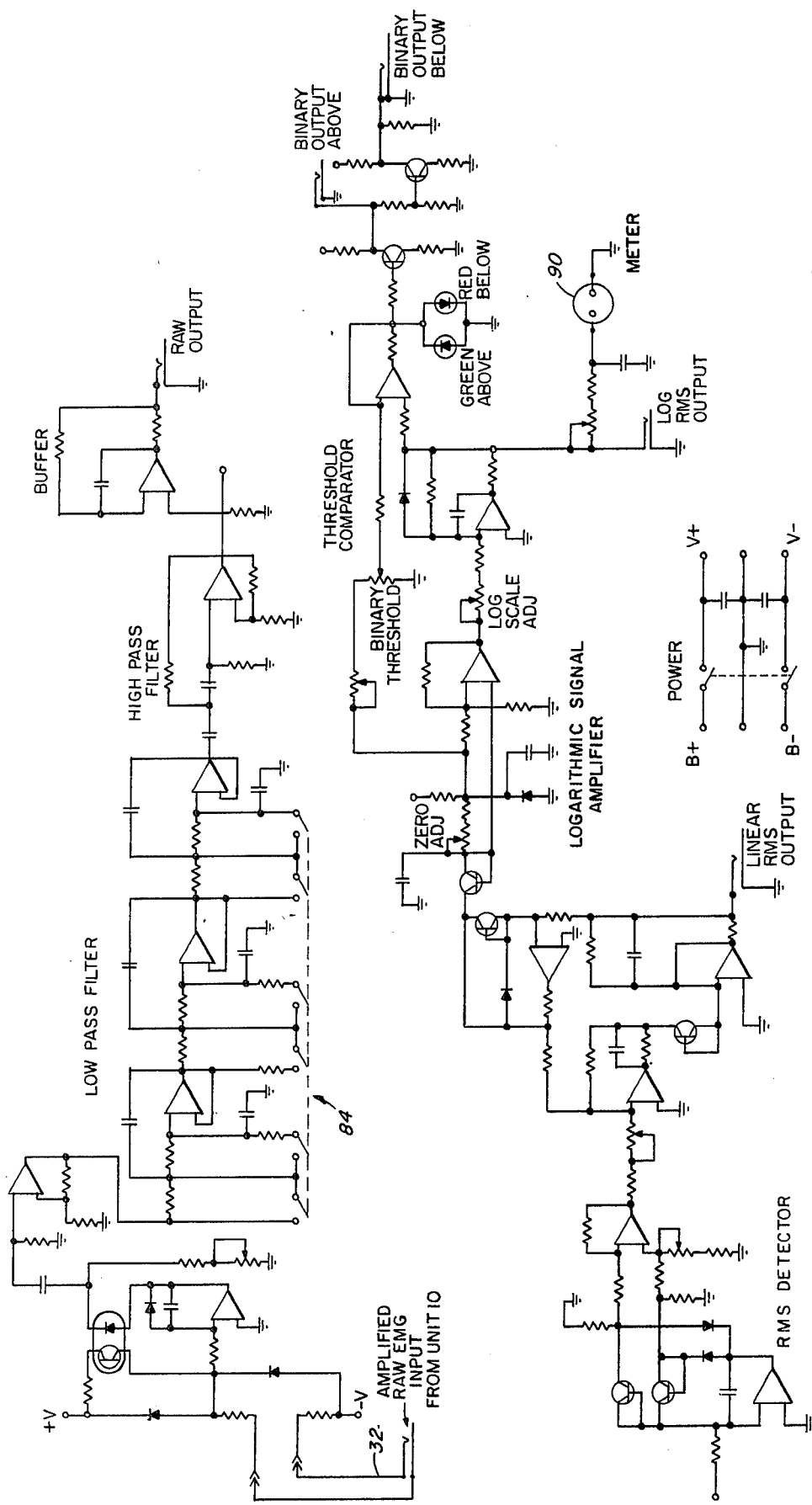
FIG. 4 is a schematic diagram of the circuitry employed in the central processor.

The central processor 12 is provided with selective bandpass filter 84 by means of which a wide or narrow bandpass may be set into the circuit, and this would normally be determined by the muscle area being monitored, whether this area is large or small. In the illustrated embodiment of FIG. 4 the bandwidth may be 100 to 1000 Hz or 100 to 200 Hz controlled by switches 86 and 88. The central processor is also provided with one meter 90, 92 for each unit, with each meter being of dual purpose in that each can be used to read out the periodic average value of the training channel or can be switched to read out the direct EMG activity at a remote location. One meter is provided to read out the RMS - EMG level for one channel while the other meter is provided to read out an integrated value of the first meter or, optionally, to read out the RMS - EMG level of the second channel. Integrator functions are also provided for evaluation purposes during training sessions with patients and selectible time periods for integration may be varied through a range of ten seconds, one minute or up to ten minutes, for example. Using two portable units 10, two separate sites may be monitored simultaneously with one used with a primary training channel and the other used as a control channel. Using a sufficiently long lead 36 for each unit, remote monitoring can be carried out with the subject located in a room separate from the central processor which may be monitored by a physician, clinician, or the like.

The dual system may be used to advantage in a number of therapeutic applications. For example, in physical medicine, one of the major problems with EMG biofeedback is the learning of differential control of opposing muscles. Often the signal from the muscle to be exercised is masked by tension in another muscle group. Using a dual system of the sort disclosed herein, both muscle sites may be monitored and set to provide feedback only when two conditions are met, namely, when the training muscle group increases in tension and a control muscle group stays below a preset threshold level. Also, in relaxation training the dual system may be used to monitor muscle activity at two sites simultaneously with independent and/or strip chart recorder output for each channel available. Such procedures help document the extent to which the training of one muscle group is affecting other muscle groups. By employing the integrator function of the central processor, greater flexibility of operation is provided since the instrument is capable of generating feedback data both in real time for monitoring instant changes in the EMG level, or delayed indications for monitoring EMG activity over an extended period of time. The real time indications provide immediate feedback of EMG changes to facilitate learning. However, delayed types of feedback, in particular, feedback which gives the subject a periodic score or value, are useful to motivate the learner and to keep a record of his progress. The integrator of the processor 12 is able to provide such data by indicating the average level of EMG activity over a selectible time period.

The processor 12 includes circuitry for carrying out true RMS processing of the preconditioned signals from the individual units 10. The RMS circuitry performs mathematical computations of the incoming signals, measuring the energy content of the signals, and does so in an extremely precise fashion so as to allow for quicker and more accurate response. RMS measuring of the signals is significantly superior to other forms of measurement techniques commonly used, such as averaging techniques, which typically involve an error factor in the range of 30% to 100% and sometimes more. When an individual is learning biofeedback techniques, it is highly desirable to obtain a feedback signal as soon as possible after the event originating the signal has occurred. Using conventional averaging circuitry the needle on the measuring gauge tends to bounce, particularly where there is a wide swing in the signal. EMG work in particular demands a fast response for optimum training results. By using a logarithmically calibrated meter and RMS measuring circuits, erratic motion of the needle is controlled.

The individual portable units 10 will be seen to be provided with what may be termed a front end portion, which is utilized both by the unit 10 when it is used by itself, and by the processor 12 when the unit is connected to the processor. The front end portion of the unit provides preconditioning of the monitored signal such that the monitored signals may be utilized either by the portable unit 10 or by the central processor 12, depending upon the operating mode. The front end circuitry always preconditions the signal by amplification and filtering to a level in excess of the requirements of the individual unit 10 although matched to the requirements of the central processor so that the front end is compatible with both the processor 12 as well as the feedback portion of the portable unit 10. This front end portion of the unit 10 includes the high gain amplifier, the prefiltering circuitry and the programmable gain functions. The high sensitivity and dynamic range of the front end is such as to be compatible with a high or low grade processor.

Figure 5:
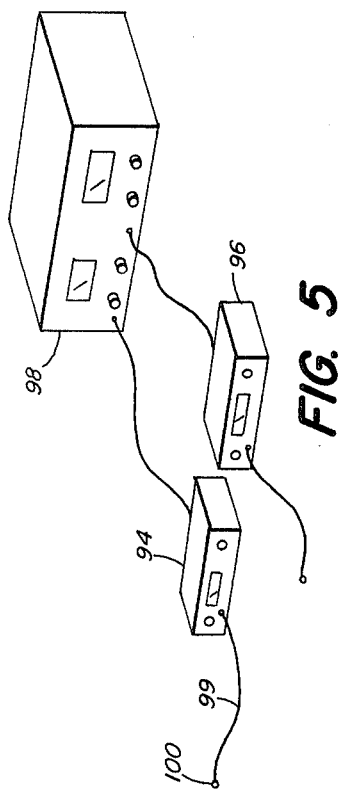
FIG. 5 is a block diagram showing another embodiment of the invention.

While the illustrated embodiments in FIGS. 1 through 4 are directed towards partitioned biofeedback monitoring systems useful for EMG work, the same technique may be employed for other biofeedback work, such as EEG or thermal training. In FIG. 5 there is illustrated a system which may be used for thermal training applications and includes a pair of portable units 94 and 96 connected to a central processor 98. Each of the portable units 94 and 96 is provided with a lead 98 terminating in a temperature sensor or transducer 100. Typically the sensor 100 directly converts the monitored temperature into a voltage which is preconditioned by the front end of the units 94 and 96. Here again the preconditioning capability of the front end of each of the units 94 and 96 exceeds the requirements of the feedback portion of the units 94 and 96 but is compatible with the requirements of the processor 98.

Having thus described the invention, what we claim and desire to obtain by Letters Patent of the United States is:

1. Apparatus for use in the biofeedback training of a subject either as an independent apparatus or in operative conjunction with other complementary and separately housed apparatus, comprising:
  (a) a relatively small, portable housing,
  (b) first stage biofeedback circuit means in said housing for processing signals fed thereto to a first level of conditioning,
  (c) power means connected to said circuit means for energization thereof,
  (d) first connection means connectable to said subject and to said circuit means to provide input signals thereto,
  (e) second connection means connectable to said circuit means and to said other apparatus whereby input signals processed by said circuit means to said first level of conditioning are transferred to said other apparatus as an input thereto for processing to a second level of conditioning,
  (f) sensory signal generating means in said portable housing connected to and responsive to said first stage circuit means and adapted to produce sensory signals as a feedback to said subject,
  (g) said circuit means including first stage electronic filtering means adapted to pass signals only within a predetermined bandpass, and
  (h) control means in said housing for varying said bandpass.

2. Apparatus, according to claim 1, including optical isolating means in said second connection means for electro-optically transmitting signals to said other apparatus.

3. Apparatus, according to claim 1, wherein said circuit means includes sensing means adapted to detect a faulty contact between said first connection means and said subject.

4. Apparatus, according to claim 1, wherein said circuit means includes power level sensing means connected to said power means and adapted to detect low power in said power means.

5. Apparatus, according to claim 1, wherein said sensory signal-generating means includes a loudspeaker and switch means connected to said loudspeaker and to said circuit means for selectively changing the audio output of said speaker.

6. Apparatus, according to claim 1, including a logarithmic meter connected to said circuit means to provide a visible display of the feedback signal.

7. A system for use in the biofeedback training of a subject comprising:
  (a) at least one first separate processor, and
  (b) a second processor separate from said first processor and detachably connectable thereto,
  (c) said first processor adapted to selectively function both independently of and dependently upon said second processor,
  (d) said first processor including signal preconditioning circuit means for preconditioning signals fed thereto to a first level of conditioning,
  (e) said first processor including relatively simple biofeedback processing circuits,
  (f) said second processor including relatively complex biofeedback processing circuitry for conditioning signals from said first processor to a second level of conditioning,
  (g) said preconditioning circuit means being compatible with the processing circuitry of both said first and second processors,
  (h) separate power means connected to said first and second processors, respectively, for independent energization thereof,
  (i) first connector means connectable to said subject and to said preconditioning means in said first processor to provide input signals thereto,
  (j) second connector means selectively connectable to said preconditioning means in said first processor and to said second processor whereby preconditioned signals at a first level of conditioning are transferred to said second processor as an input thereto for processing to a second level of conditioning,
  (k) each of said first and second processors including separate sensory feedback generating means connected to and responsive to said processing circuitry and adapted to produce sensory feedback to said subject.

8. A system, according to claim 7, including optical isolating means in said second connector means for electro-optically transmitting signals to said second processor.

9. A system, according to claim 7, wherein said preconditioning circuit means includes electronic filtering means adapted to pass signals only within a predetermined bandpass.

10. A system, according to claim 9, including control means for varying said bandpass.

11. A system, according to claim 9, including a jack mounted to said first processor and detachably connectable to said first connector means, said power means including a rechargeable battery and a recharging circuit connected to said jack whereby said battery can be recharged only when said first connector means is disconnected from said jack.

12. A system, according to claim 7, wherein said preconditioning circuit means includes sensing means adapted to detect a faulty contact between said first connection means and said subject.

13. A system, according to claim 7, wherein said preconditioning circuit means includes power level sensing means connected to said power means and adapted to detect low power in said power means.

14. A system, according to claim 7, wherein said sensory signal-generating means includes a loudspeaker and switch means connected to said loudspeaker and to said circuit means for selectively changing the audio output of said speaker.

15. A system, according to claim 7, wherein at least said simple processing circuitry includes a logarithmic meter to provide a visible display of the feedback signal.

* * * * *